United States Patent
Kraft et al.

(10) Patent No.: US 9,897,527 B2
(45) Date of Patent: Feb. 20, 2018

(54) OPERATING MEDIUM FOR A CONDENSATION NUCLEUS COUNTER FOR INTERNAL COMBUSTION ENGINE EXHAUST GASES

(71) Applicant: AVL LIST GMBH, Graz (AT)

(72) Inventors: Martin Kraft, Vienna (AT); Alexander Bergmann, Graz (AT)

(73) Assignee: AVL LIST GMBH, Graz (AT)

( * ) Notice: Subject to any disclaimer, the term of this patent is extended or adjusted under 35 U.S.C. 154(b) by 0 days.

(21) Appl. No.: 14/912,487

(22) PCT Filed: Aug. 28, 2014

(86) PCT No.: PCT/EP2014/068267
§ 371 (c)(1),
(2) Date: Feb. 17, 2016

(87) PCT Pub. No.: WO2015/028553
PCT Pub. Date: Mar. 5, 2015

(65) Prior Publication Data
US 2016/0202166 A1    Jul. 14, 2016

(30) Foreign Application Priority Data
Aug. 30, 2013   (AT) ............................. A 50537/2013

(51) Int. Cl.
*G01N 15/06* (2006.01)
*G01N 15/00* (2006.01)

(52) U.S. Cl.
CPC ... *G01N 15/065* (2013.01); *G01N 2015/0046* (2013.01)

(58) Field of Classification Search
CPC ..................... G01N 15/065; G01N 2015/0046
See application file for complete search history.

(56) References Cited

U.S. PATENT DOCUMENTS

| 4,144,040 | A  | 3/1979  | Claes et al. |
| 4,790,650 | A  | 12/1988 | Keady |
| 6,469,781 | B1 | 10/2002 | Katz et al. |
| 7,777,867 | B2 | 8/2010  | Hopke et al. |

(Continued)

FOREIGN PATENT DOCUMENTS

| RU | 2237882    | 10/2004 |
| WO | 0131312    | 5/2001  |
| WO | 2012142297 | 10/2012 |

OTHER PUBLICATIONS

Magnusson, Lars-Erik, et al. "Correlations for vapor nucleating critical embryo parameters." Journal of Physical and Chemical Reference Data 32.4 (2003): 1387-1410.*

(Continued)

*Primary Examiner* — Harshad R Patel
*Assistant Examiner* — Punam Roy
(74) *Attorney, Agent, or Firm* — Dykema Gossett PLLC

(57) ABSTRACT

An n-alkane with the general chemical formula $C_nH_{2n+2}$ with an ordinal number n of ten, eleven or twelve is used as operating medium (7) for a condensation nucleus counter for exhaust gases from internal combustion engines (4) by which individual particles contained in the exhaust gas can be counted.

6 Claims, 1 Drawing Sheet

(56) References Cited

U.S. PATENT DOCUMENTS 8,208,132 B2    6/2012  Huetter et al.

OTHER PUBLICATIONS

Lee, Doh-Won, et al. "Comparison of experimental and theoretical heterogeneous nucleation on ultrafine carbon particles." The Journal of Physical Chemistry B 107.50 (2003): 13813-13822.*
Smorodin, Vladimir Y., and Philip K. Hopke. "Relationship of heterogeneous nucleation and condensational growth on aerosol nanoparticles."Atmospheric research 82.3 (2006): 591-604.*
Mavliev, Rashid, et al. "Experimental studies of heterogeneous nucleation in the turbulent mixing condensation nuclei counter." The Journal of Physical Chemistry B 108.14 (2004): 4558-4564.*
McGraw, Robert, Jian Wang, and Chongai Kuang. "Kinetics of heterogeneous nucleation in supersaturated vapor: Fundamental limits to neutral particle detection revisited." Aerosol Science and Technology 46.9 (2012): 1053-1064.*
English Abstract of RU 2237882, Oct. 2004.

* cited by examiner

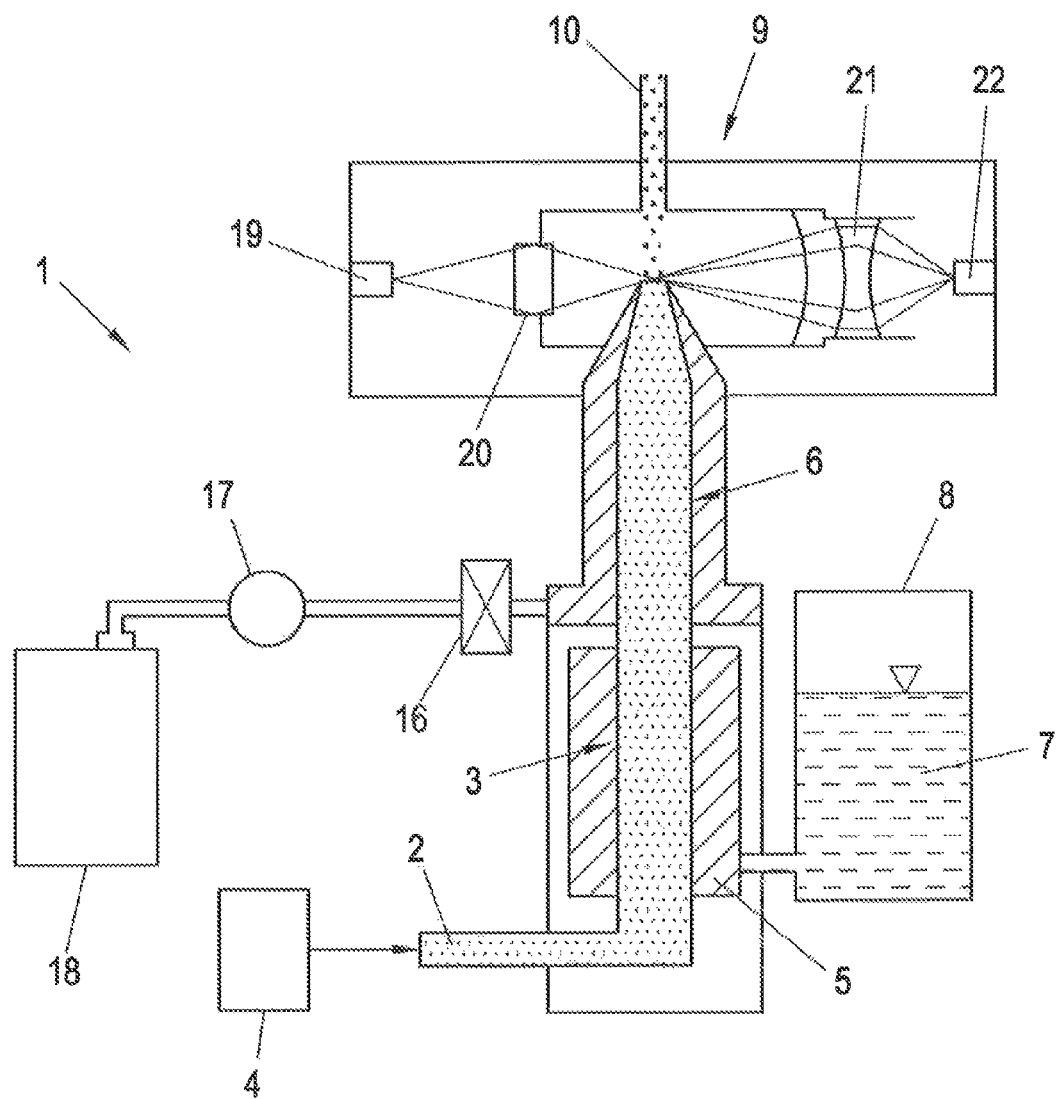

OPERATING MEDIUM FOR A CONDENSATION NUCLEUS COUNTER FOR INTERNAL COMBUSTION ENGINE EXHAUST GASES

This application is a U.S. national stage of PCT/EP2014/068267, filed 28 Aug. 2014 which was based on Austrian Application No. A50537/2013, filed 30 Aug. 2013. All priorities are claimed.

BACKGROUND OF THE INVENTION

The present invention relates to an operating medium for a condensation nucleus counter for internal exhaust gases from combustion engines and a condensation nucleus counter with an operating medium according to the invention.

Exhaust gases from an internal combustion engine contain solid particles in the nm range which are too small for it to be possible to detect them directly by optical means. In order to make such solid particles measurable, so-called condensation nucleus counters are frequently used in which the exhaust gas is passed through a supersaturated atmosphere. The supersaturated atmosphere is generated for example by saturating the exhaust gas with vapors from an operating medium and subsequently cooling it. The solid particles then serve as condensation nuclei onto which the supersaturated operating medium is condensed, which leads to a growth of the condensation nuclei. Such a condensation nucleus counter is known for example from U.S. Pat. No. 4,790,650 A or WO 12/142297 A1. The size of the solid particles from which this condensation process takes place is dependent upon the supersaturation and is designated as the Kelvin diameter. The smaller the Kelvin diameter is for a specific supersaturation, the smaller the solid particles can be, which lead to the condensation of operating medium. According to guidelines, for example statutory requirements, for exhaust gas the particle size range from greater than 20 nm, typically 23 nm, to 2.5 μm is to be detected and the exhaust gas is to be conditioned to a temperature of <35° C. before the saturator. Due to the condensation the size of the particles increases (to approximately 5 μm), and the particles can then be individually optically detected, for example with optical particle counters based on scattered light. For the detection and counting of individual particles, the particles must have a sufficient size in the μm range.

The currently standard operating medium for condensation nucleus counters for the measurement of solid particles in exhaust gases from internal combustion engines is 1-butanol (n-butanol), as described for example in EP 2 208 983 B1. The primary disadvantage of this operating medium is its chemical reactivity with the exhaust gas. With acidic exhaust gas components the alcohol forms esters which as a consequence are enriched in the wick elements of the condensation nucleus counter and lead to a reduction of the gas saturation. A further practical disadvantage is a flashpoint of ~37° C., that is to say, in the range of the desired temperature.

In WO 01/31312 A1 an abundance of possible operating media for a condensation nucleus counter are examined, wherein the main focus in this case is aimed at the detection of very small molecules (smaller than 3 nm) for the chemical analysis of chemical substances. In order in this case to achieve the smallest possible detection limit, the system is geared to the smallest possible Kelvin diameters. Soot or other exhaust gas particles which are significantly larger than the molecules studied in WO 01/31312 A1 do not play any part here. In this case it is stated that glycol is the most suitable operating medium for such applications because it allows the smallest Kelvin diameters. In addition to a large number of further chemical substances which are conceivable in principle, alkanes, and specifically hexane, heptane, octane and nonane, are mentioned as operating medium, but these all enable poorer Kelvin diameters and therefore are not described in WO 01/31312 A1 as preferred operating medium for these applications.

Furthermore WO 01/31312 A1 describes a method for selecting an operating medium from a group of chemical substances (for example alkanes) as the most suitable operating medium. For this purpose the relative dielectric constant $\in_r$ of the operating medium should be used and the operating medium with the highest dielectric constant in the chemical group are selected. The relative dielectric constant is a parameter which is known for the individual substances, for example from corresponding tables or specifications. Also by this criterion alkanes are categorized according to WO 01/31312 A1 as the least suitable operating media, because the relative dielectric constant thereof at $\in_r \sim 2$ is lower by more than one order of magnitude than that of the preferred operating medium glycol ($\in_r \sim 41$) or glycerol ($\in_r \sim 47$).

An alternative used in the field of atmospheric research is the use of water as operating medium (see also for example WO 01/31312 A1). However, for the present application in exhaust gases from internal combustion engines water cannot be used, since water does not grow sufficiently reliably on soot particles in the exhaust gas. In addition, because of the high diffusivity of water vapor in air, water would necessitate a fundamentally different system whereby water cannot be used in conventional condensation nucleus counters for exhaust gas. Thus water does not constitute a reasonable alternative as operating medium for the present application.

The use of perfluorinated compounds, in particular perfluoro-N-trialkylamines (for example perfluoro-N-tributylamine, Fluorinert FC-43), as operating medium for a condensation nucleus counter is known for example from U.S. Pat. No. 7,777,867 B2, Advantages of this operating medium are the excellent chemical inertness and the non-combustibility. However, a disadvantage of these operating media is the high density due to which conveying (and corresponding gas saturation) in condensation nucleus counters of specific design, for example with a vertical wick element, is not possible, which makes this compound usable only with limitations. Moreover, perfluorinated compounds are expensive and also potentially environmentally harmful, which makes the handling of such compounds difficult.

RU 2 237 882 C1 describes a method for determining the particle concentration of aromatic compounds in a gas by means of a nephelometer, wherein the aromatic compounds are initially converted by means of ozone to condensation nuclei which are then enlarged to particles by the use of tetradecane or heptadecane as operating medium by condensation. However, the tetradecane and heptadecane described therein are unsuitable as operating medium for a condensation nucleus counter for the particle measurement in exhaust gases from internal combustion engines, since in the desired operating temperature range they have a vapor pressure which is too low by an order of magnitude in order to produce an atmosphere which is sufficiently saturated or supersaturated with operating medium which is necessary for proper functioning. An increase in the operating temperature in order to achieve a sufficient saturation would be technically possible but, firstly, would not comply with the statutory and normative requirements of such devices for particle measurement in exhaust gases from internal combustion engines and, secondly, operating temperatures in the range of the flashpoints of the respective substances would be necessary, which would constitute a substantial safety hazard. Apart from that, in the operating temperature range of the condensation nucleus counter these alkanes are solid or do not have sufficiently low viscosity, which likewise rules out use thereof for the desired application.

Therefore an object of the present invention is to provide a suitable operating medium for a condensation nucleus counter for internal combustion engine exhaust gases.

SUMMARY OF THE INVENTION

This object is achieved by the use of n-alkane with the general chemical formula $C_nH_{2n+2}$ with an ordinal number n of ten, eleven or twelve as operating medium.

In WO 01/31312 A1 the n-alkanes with the ordinal number n of six (hexane) to nine (nonane) have the poorest characteristics by comparison with the other operating media referred to, and within the group of alkanes those with a higher ordinal number have poorer characteristics, for example a greater Kelvin diameter, than alkanes with a lower ordinal number. However, the method proposed in WO 01/31312 A1 for selection of the operating medium is unsuitable in particular for alkanes, since the different alkanes have very similar dielectric constants, which makes a reliable selection on the basis of this criterion impossible. If the specified criterion is nevertheless applied to the group of alkanes, then as preferred operating medium, for example cyclohexane with a relative dielectric constant of 2.024 would be preferred to the n-alkanes with relative dielectric constants below that.

Surprisingly, however n-alkanes with the ordinal number n of ten (decane, $H_{10}C_{22}$), eleven (undecane, $C_{11}H_{24}$) and twelve (dodecane, $C_{12}H_{26}$) are most suitable specifically for exhaust gases from internal combustion engines, which was not foreseeable on the basis of the disclosure of WO 01/31312 A1. The reason for this is that alkanes with the ordinal number ten (decane), eleven (undecane) and twelve (dodecane) at the desired operating temperatures of the condensation nucleus counter, typically −20° C. to 50° C., are liquid and are substantially unreactive relative to the exhaust gas components, in particular relative to organic acids, water, etc., and do not participate in any chemical reaction with exhaust gas components, for example esterification, etc. Furthermore, alkanes do not generally mix with water, for example in the form of condensate in the exhaust gas, which prevents or at least reduces the contamination of the operating medium. In addition, such alkanes have a sufficiently high flashpoint at room temperature, in order to prevent the formation of ignitable or explosive alkane/air mixtures at room temperature, which would necessitate expensive safety and/or explosion protection measures. Furthermore, with these alkanes no phase transitions, for example liquid-gas transitions, occur in the desired operating temperature range from −20° C. to 50° C. Furthermore, the toxicity of such alkanes is lower than the toxicity of the fuels used in the internal combustion engine, so that the handling of the operating medium can be simplified. Last but not least, these alkanes also have a sufficiently high vapor pressure in order to facilitate the growth and thus also ensure the reliable condensation on exhaust gas solid particles, in particular soot.

BRIEF DESCRIPTION OF THE FIGURE

The present invention is explained in greater detail below with reference to FIG. 1, which shows by way of example, schematically and without limitation, a condensation nucleus counter for exhaust gases from internal combustion engines.

DETAILED DESCRIPTION OF THE FIGURE

FIG. 1 shows schematically a condensation nucleus counter 1 with a feed line 2 for exhaust gas from an internal combustion engine 4, which is extracted for example from the exhaust pipe of the internal combustion engine 4. The exhaust gas may also be diluted exhaust gas. The exhaust gas enters a temperature-controlled saturation unit 3, preferably temperature-controlled in the operating temperature range from −20° C. to 50° C., which for example comprises a porous saturation element 5 to which liquid operating medium 7 is delivered from an operating medium reservoir 8. The exhaust gas flows through the saturation element 5 and is moistened by the operating medium 7. The degree of saturation or supersaturation of the operating medium 7 in the exhaust gas, and thus the achievable size of the enlarged particles, can be set by means of the temperature in the saturation unit 3, and optionally by means of the temperature difference relative to the subsequent cooler condensation unit 6. In the subsequent condensation unit 6, which is cooled by suitable cooling agent, the operating medium 7 in the exhaust gas condenses onto the solid particles contained in the exhaust gas. The particles which are enlarged in this way, preferably in the μm range, can then be counted in a particle counter 9. The exhaust gas is discharged again via a discharge line 10.

From the cooled condensation unit 6 water is returned into a receiving tank 18 by means of a filter 16 and a pump 17. Any operating medium 7 dripping off passes back directly into the saturation unit 3.

The particle counter 9 here comprises a laser diode 19, of which the light is focused by means of a focusing unit 20 onto the outlet point of the particle-laden exhaust gas stream supersaturated with operating medium and is collected and delivered by means of a collector 21 to a detector 22. Thus each individual particle coming out at the outlet point can be detected and counted and thus the total concentration of the particles in the exhaust gas can be detected.

Decane ($C_{10}H_{22}$), undecane ($C_{11}H_{24}$) or dodecane ($C_{12}H_{26}$), or corresponding binary or ternary mixtures of decane ($C_{10}H_{22}$), undecane ($C_{11}H_{24}$) or dodecane ($C_{12}H_{26}$) can be used as operating medium 7.

The invention claimed is:

1. A condensation nucleus counter for counting individual soot particles in exhaust gas from an internal combustion engine, comprising:
    a saturation unit containing a saturation element,
    means for delivering an operating medium to the saturation element, said operating medium consisting of at least one n-alkane of general formula $C_nH_{2n+2}$, wherein n is 10, 11 or 12,
    a feed line for delivering exhaust gas containing individual soot particles to the saturation unit for moistening by the operating medium,
    a condensation unit wherein said operating medium condenses on said individual soot particles in the exhaust gas to enlarge said individual soot particles, and
    a particle counter in which said enlarged individual soot particles in the exhaust gas are counted.

2. A method of counting individual soot particles contained in exhaust gas from an internal combustion engine, said method comprising the steps of:

(a) contacting the exhaust gas containing soot particles with an operating medium consisting of at least one n-alkane having a general formula $C_nH_{2n+2}$, wherein n is 10, 11 or 12, so that the soot particles become moistened with the operating medium, (b) cooling the exhaust gas with moistened soot particles from step (a) so that the operating medium in the exhaust gas condenses on the soot particles and enlarges the soot particles, and (c) counting the enlarged soot particles in the exhaust gas of step (b).

3. The method of claim 2, wherein in step (a) the exhaust gas containing soot particles is passed through a porous saturation element containing the operating medium.

4. The method of claim 3, including a step (a1) of delivering operating medium to the porous saturation element from a reservoir.

5. A condensation nucleus counter for counting individual soot particles in exhaust gas from an internal combustion engine, comprising:

a porous saturation element containing an operating medium consisting of at least one n-alkane of general formula $C_nH_{2n+2}$, wherein n is 10, 11 or 12, a feed line for delivering exhaust gas containing individual soot particles to the porous saturation element for moistening by the operating medium, a condensation unit wherein said operating medium condenses on said individual soot particles in the exhaust gas to enlarge said individual soot particles, and a particle counter in which said enlarged individual particles in the exhaust gas are counted.

6. A condensation nucleus counter for counting individual soot particles in exhaust gas from an internal combustion engine, comprising:

a saturation unit containing a saturation element, reservoir containing an operating medium consisting of at least one n-alkane of general $C_nH_{2n+2}$, when n is 10, 11 or 12, said reservoir including a delivery line which is connected to the saturation unit for delivering said operating medium to the saturation element, a feed line for delivering exhaust gas containing individual soot particles to the saturation unit for moistening by the operating medium, a condensation unit wherein said operating medium condenses on said individual soot particles in the exhaust gas to enlarge said individual soot particles, and a particle counter in which said enlarged individual soot particles in the exhaust gas are counted.

* * * * *